(12) United States Patent
Lunn et al.

(10) Patent No.: US 7,833,218 B2
(45) Date of Patent: Nov. 16, 2010

(54) CATHETER WITH REINFORCING LAYER HAVING VARIABLE STRAND CONSTRUCTION

(75) Inventors: Peter A. Lunn, Beverly, MA (US); Kenneth D. Warnock, Jr., Manchester-by-the-Sea, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 172 days.

(21) Appl. No.: 12/103,462

(22) Filed: Apr. 15, 2008

(65) Prior Publication Data

US 2008/0262472 A1     Oct. 23, 2008

Related U.S. Application Data

(63) Continuation-in-part of application No. 11/736,247, filed on Apr. 17, 2007, now abandoned.

(51) Int. Cl.
A61M 25/00     (2006.01)
(52) U.S. Cl. .................................................... 604/526
(58) Field of Classification Search ......... 604/524–527; 600/434, 435, 585; 264/171.2; 138/123, 138/124, 129, 130, 155
See application file for complete search history.

(56) References Cited

U.S. PATENT DOCUMENTS

| 467,585 | A | 1/1892 | Struss |
|---|---|---|---|
| 2,158,266 | A | 5/1939 | Aldrich |
| 2,354,212 | A | 7/1944 | Jeckel |
| 2,362,688 | A | 11/1944 | Dunn |
| 2,494,389 | A | 1/1950 | Jeckel |
| 5,462,523 | A | 10/1995 | Samson et al. |
| 5,538,513 | A | 7/1996 | Okajima |
| 5,873,866 | A | 2/1999 | Kondo et al. |
| 5,964,971 | A | 10/1999 | Lunn |
| 6,152,912 | A | 11/2000 | Jansen et al. |
| 6,939,337 | B2 | 9/2005 | Parker et al. |
| 2003/0176849 | A1 | 9/2003 | Wendlandt et al. |
| 2007/0049903 | A1* | 3/2007 | Jansen et al. ........... 604/526 |

FOREIGN PATENT DOCUMENTS

| EP | 1068876 | 7/2000 |
|---|---|---|
| EP | 1787674 | 5/2007 |
| WO | WO2006/016481 | 2/2006 |
| WO | WO2007/013545 | 2/2007 |

* cited by examiner

*Primary Examiner*—Kevin C Sirmons
*Assistant Examiner*—Catherine N Witczak

(57) ABSTRACT

A catheter includes an elongate member having a braided reinforcing layer encased within a polymeric bonding layer. The reinforcing layer comprises a plurality of continuous filaments that transform from a full complement braid configuration to a partial complement braid configuration in a least one location along the catheter. Also disclosed is a method of manufacturing a braided elongate member including providing a core, forming at least one full complement braid portion with a plurality of filaments and forming at least one partial complement braid portion with a portion of the same plurality of filaments.

26 Claims, 14 Drawing Sheets

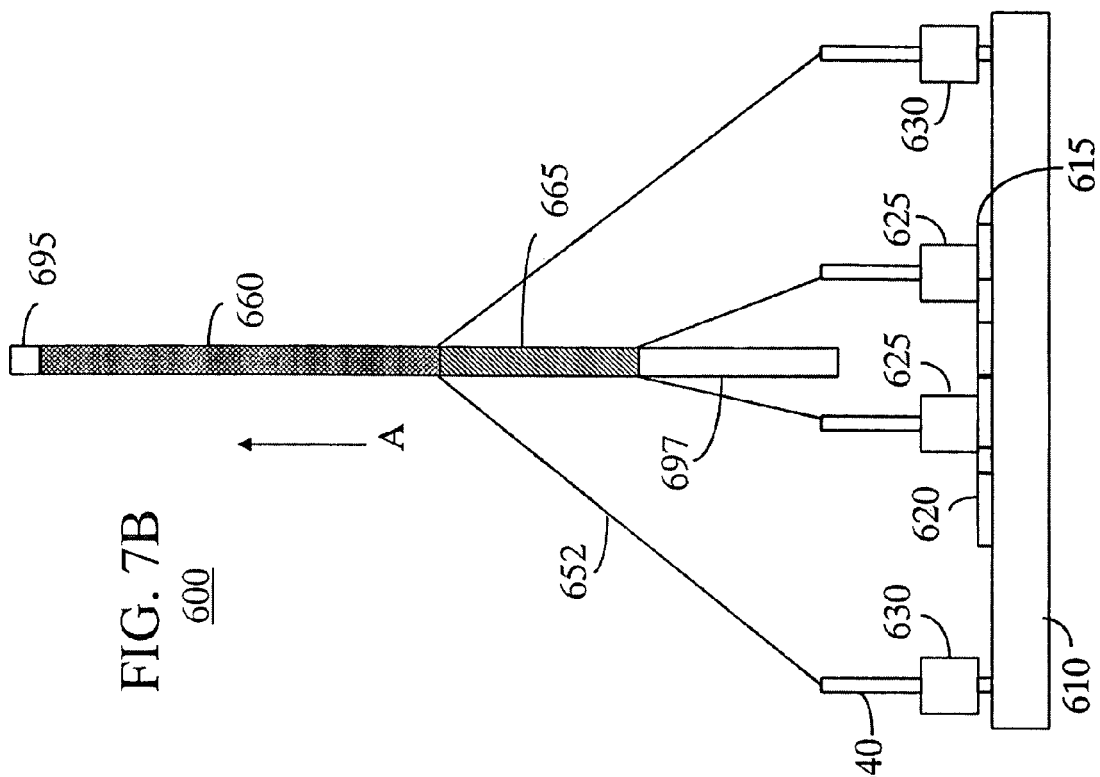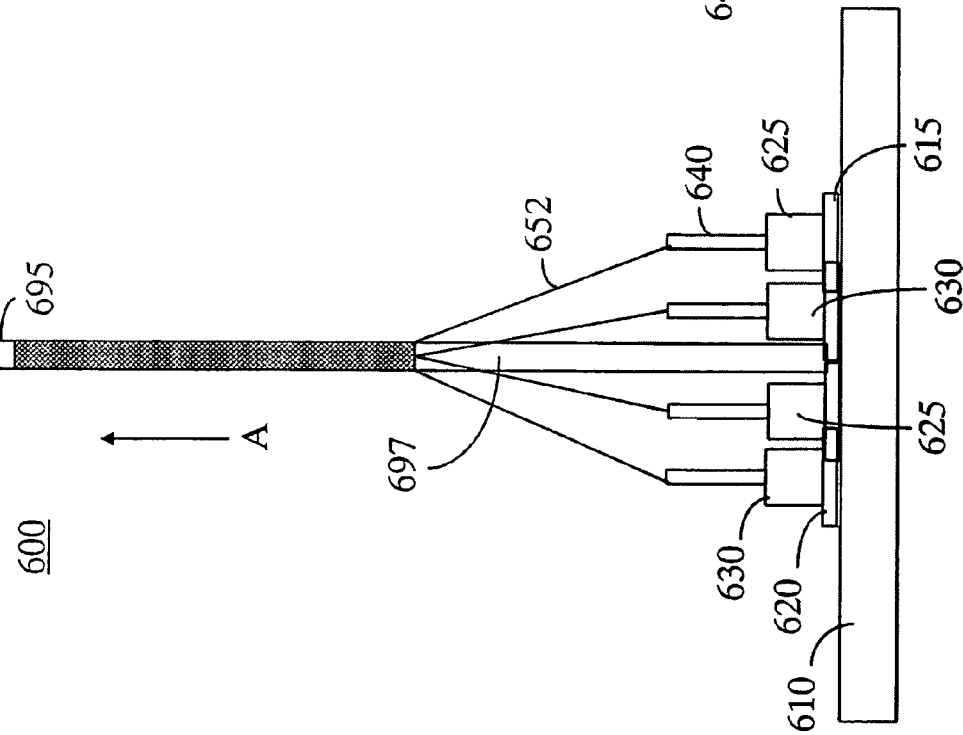

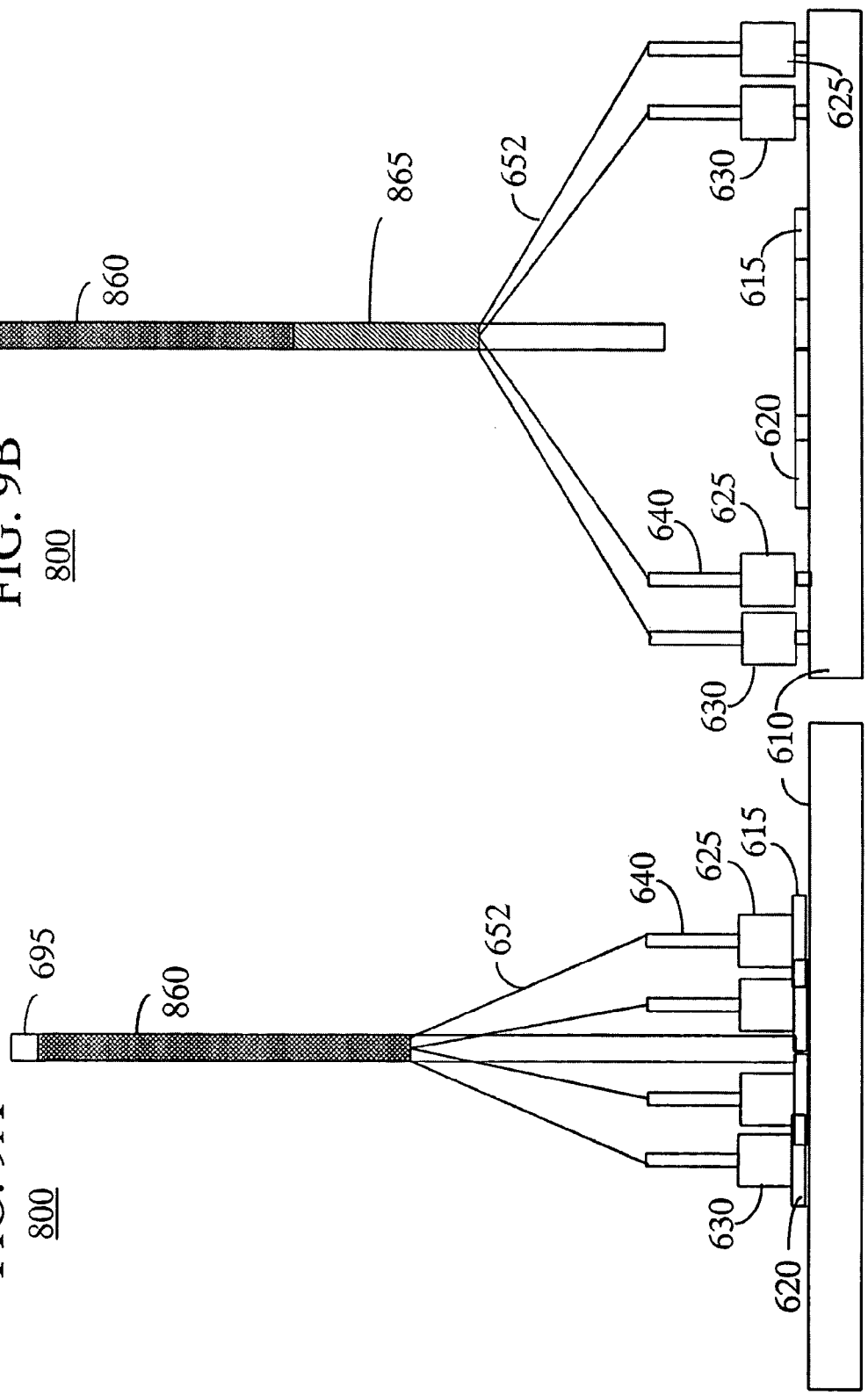

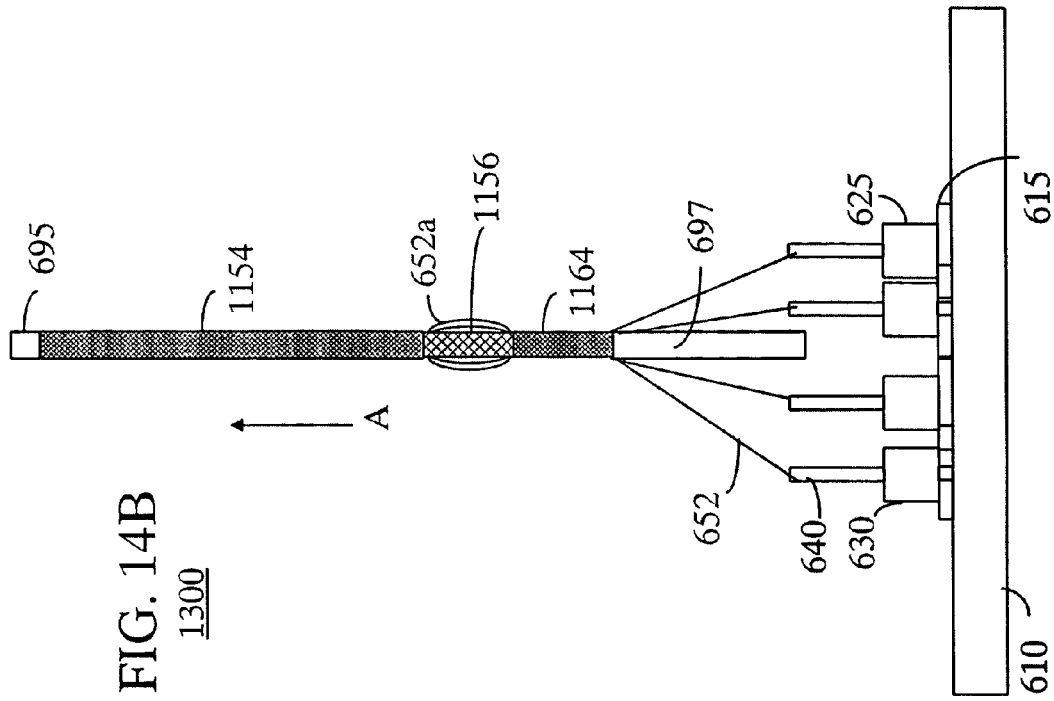
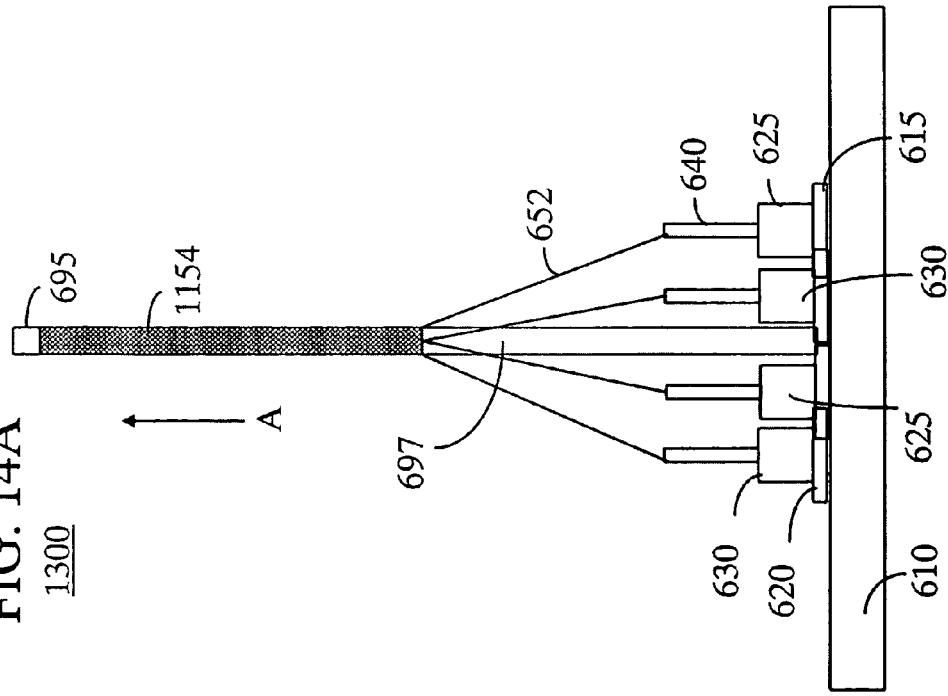

CATHETER WITH REINFORCING LAYER HAVING VARIABLE STRAND CONSTRUCTION

RELATED APPLICATIONS

This application is a continuation-in-part of and claims priority to U.S. patent application Ser. No. 11/736,247, to Kenneth Warnock Jr., filed Apr. 17, 2007.

FIELD OF THE INVENTION

This invention relates generally to medical catheters, and more particularly to the design and fabrication of catheters having a reinforcement layer that transforms from a braid to a coil.

BACKGROUND

Cardiovascular disease, including atherosclerosis, is a leading cause of death in the U.S. A number of methods and devices for treating coronary heart disease have been developed, including a broad array of catheters and minimally invasive methods for using them. Catheter-based delivery systems are routinely used to introduce stents and other medical devices into the cardiovascular system for both therapeutic and diagnostic purposes.

Typically, the catheter is inserted into the vascular system percutaneously through an artery, such as the femoral, jugular, or radial artery. The catheter is threaded through the vascular system until the distal end of the catheter is adjacent to the treatment site. The position of the catheter end may be determined by common visualization methods such as fluoroscopy or ultrasound.

In order to perform well, a catheter must have sufficient columnar strength and rigidity so that it can be pushed through the vasculature of the patient without bending back on itself or kinking. However, if it is too stiff; it may cause damage to blood vessel walls. At the same time, the catheter must be sufficiently flexible so that it can follow a winding, sometimes tortuous, path through the patient's vasculature. In order to balance the need for both flexibility and columnar strength, catheters are frequently constructed to have a relatively rigid proximal section and a more flexible distal section. Such a balanced combination also provides a catheter with good steerability, which is the ability to transmit substantially all rotational inputs from the proximal end to the distal end.

Available catheters attempt to achieve this balanced combination by using support layers of braided and/or coiled filaments within the wall of the catheter. A coiled support layer reinforces the catheter body against crushing, kinking or radial expansion from internal pressure, while adding negligible bending stiffness to the composite catheter structure. A braided support layer also provides resistance to crushing, kinking or radial expansion from internal pressure, while adding substantial torsional stiffness, and may add bending stiffness to the catheter.

The braided and/or coiled material is positioned along at least a portion of the length of the catheter. Where prior art catheters incorporate both braided and coiled support layers, the catheters are manufactured such that the braided material either overlaps or abuts the coiled material as the braided material transitions to the coiled material. One drawback to the overlapping and abutting transitions between the braid and coil is that the manufacturing process requires additional steps for joining the ends of the two types of layers. Another drawback is that such discontinuities between the different types of materials may create undesirable additional thickness and/or stiffness, or a weakness at the point of joining that affects the flexibility, steerability and kink-resistance of the catheter.

The additional torsional and bending stiffness of a braided layer is often a drawback for devices that must be flexible enough to travel tortuous vessels. Prior devices have attempted to limit or decrease the stiffness in areas along the length of the catheter by changing the pick count per inch (PPI) or changing the braid angle. However, changing PPI is done by altering the relative rates of linear motion and rotary motion on a braiding machine while the same number of filaments remains in the weave. As such, these changes are gradual changes that do not allow an abrupt change in stiffness along the catheter.

It would be desirable, therefore, to provide a catheter that overcomes these and other disadvantages.

SUMMARY OF THE INVENTION

One embodiment of the invention provides a catheter comprising an elongate catheter body having a reinforcing layer encased within a polymeric bonding layer, wherein the reinforcing layer comprises a continuous plurality of filaments forming at least one full complement braid portion and at least one partial complement braid portion.

Another embodiment of the invention provides a catheter comprising an elongate body encapsulating an elongate reinforcing layer wherein the reinforcing layer comprises a plurality of filaments extending continuously along the length of the reinforcement layer, and wherein the plurality of filaments transitions from a full complement braid configuration to a partial complement braid configuration in at least one location along the length of the reinforcement layer.

Another embodiment of the invention provides a method of manufacturing a braided elongate member. The method includes providing a core, attaching a plurality of filaments to a first end of the core, forming the plurality of filaments into at least one full complement braid portion surrounding the core and forming a portion of the plurality of filaments forming the full complement braid portion into at least one partial complement braid portion surrounding the core. The at least one full complement braid portion is transformed to the at least one partial complement braid portion through a transition region.

The present invention is illustrated by the accompanying drawings of various embodiments and the detailed description given below. The drawings should not be taken to limit the invention to the specific embodiments but are for explanation and clarity. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, which are not drawn to scale.

BRIEF DESCRIPTION OF THE DRAWINGS

FIGS. 6A to 7B are schematic illustrations of one embodiment of a braiding machine in accordance with the present invention;

FIGS. 8A to 9B are schematic illustrations of another embodiment of a braiding machine in accordance with the present invention;

FIG. 13A to 14B are schematic illustrations of another embodiment of a braiding machine in accordance with the present invention.

DETAILED DESCRIPTION

Throughout this specification, like reference numbers refer to like structures. Various types of catheters that incorporate the present invention include balloon catheters, infusion catheters, diagnostic catheters, drainage catheters, guiding catheters, introducer sheaths, laparoscopes, endoscopes and arthroscopes. The below description refers generally to a vascular treatment device though it is understood that many types of medical devices, including those listed above are encompassed by the present invention. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Generally, as will be described below, the catheters of the present invention provide an elongated shaft having variable stiffness along the length of the shaft. The variable stiffness of the shaft is provided by a reinforcing layer that is either braided or coiled. The braided sections provide the shaft with increased pushability, torquability and kink resistance. In contrast, the coiled sections provide the shaft with lower stiffness to allow the more distal ends of the shaft to traverse the vasculature. Exemplary embodiments of the braided and coiled elongate member and the manufacture of the braided and coiled elongated member are described below.

Figure 1:
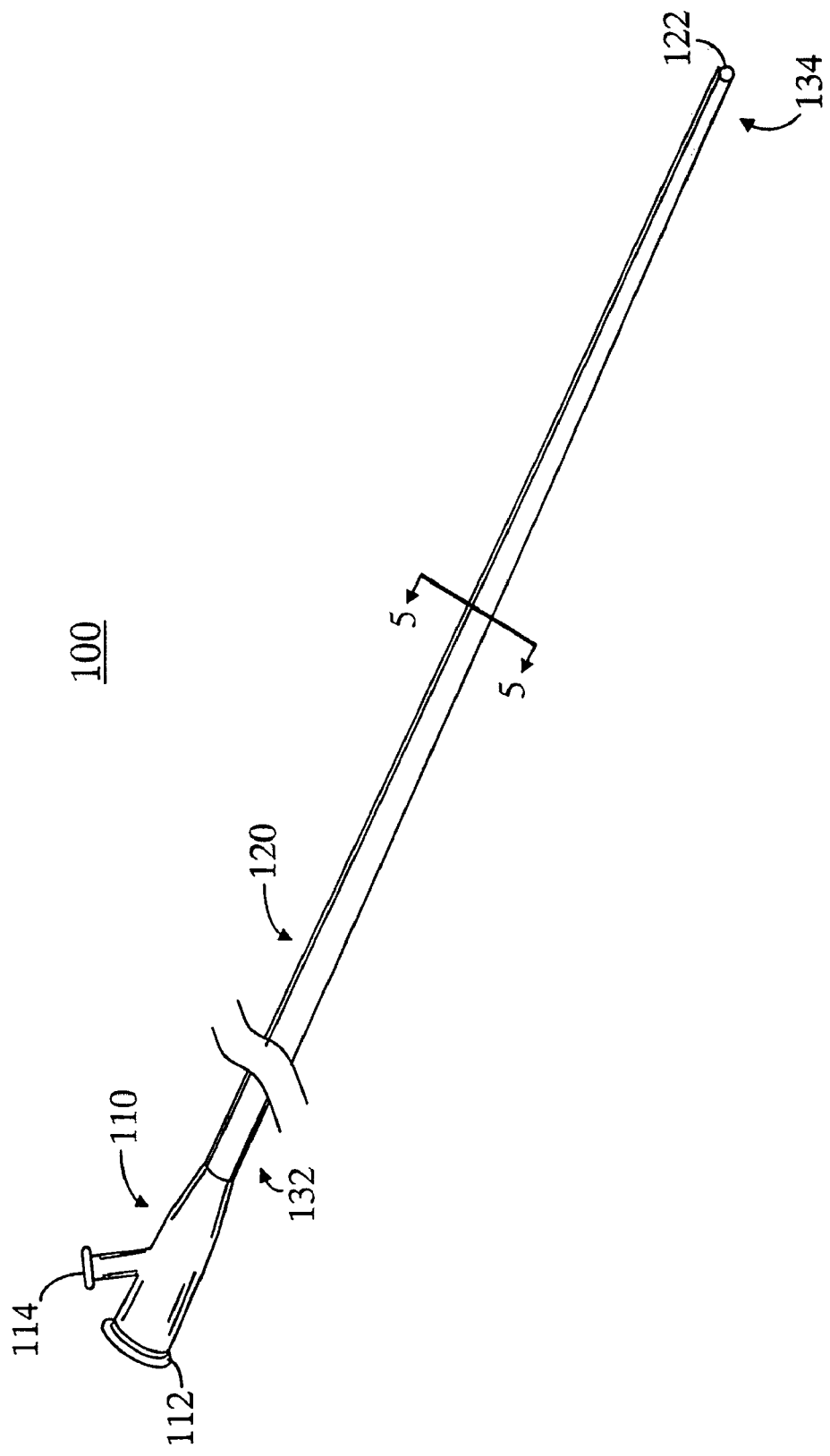
FIG. 1 shows a vascular treatment device in accordance with the present invention.

FIG. 1 illustrates a vascular treatment device 100 made in accordance with the present invention. Vascular treatment device 100 includes proximal fitting 110 attached to a proximal end of catheter body 120. Proximal fitting 110 includes end port 112 and side port 114. Proximal fitting 110 may be any fitting suitable for providing port access to catheter body lumen 122 during treatment. Proximal fittings are well known in the art and will not be discussed further.

Figure 5:
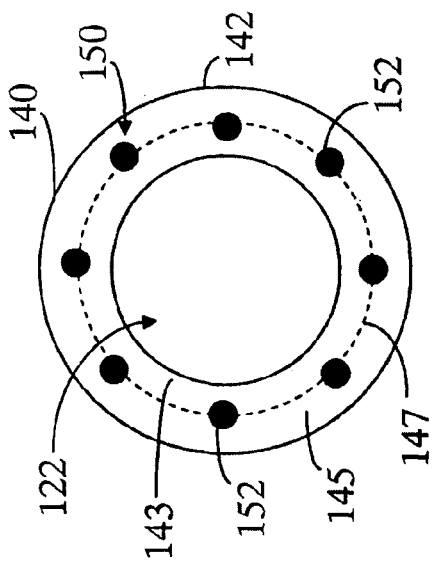
FIG. 5 shows a cross-section of the vascular treatment device of FIG. 1 taken along line 5-5.

Catheter body 120 has a proximal end 132 connected to proximal fitting 110 and a distal end 134. Referring now to FIG. 5, illustrated is a cross section of catheter body 120 taken along line 5-5 of FIG. 1. Catheter body 120 includes a catheter wall portion 140 defining lumen 122. Catheter wall portion 140 includes a polymeric bonding layer 142 and a reinforcing layer 150. Polymeric bonding layer 142 encases the reinforcing layer 150. The reinforcing layer 150 has a higher modulus of elasticity than the polymeric bonding layer that it is encased within. In one embodiment, polymeric bonding layer 142 is composed of two layers of polymeric material, a first (inner) layer 143 and a second (outer) layer 145. Inner layer 143 and outer layer 145 are fused together to encase reinforcing layer 150. The junction between inner layer 143 and outer layer 145 is delineated by dashed line 147. Polymeric bonding layer 142 may be manufactured from any suitable polymer or polymers such as, for example, polyamide, polyimide, polyolefins such as polyethylene or polypropylene, polyurethane, polyethylene block amide copolymer (PEBA), or fluoropolymers such as polytetrafluoroethylene (PTFE), fluorinated ethylene propylene (FEP), or perfluoroalkoxy (PFA). In one embodiment, polymeric bonding layer 142 is adhered to reinforcing layer 150 by adhesive. In another embodiment, polymeric bonding layer 142 includes a first (inner) layer 143 and a second (outer) layer 145 that are adhesively or thermally bonded together around reinforcing layer 150 during the manufacturing process, as will be known to one of ordinary skill in the art of catheters.

Reinforcing layer 150 is a braided and coiled layer composed of a plurality of metallic or polymeric filaments 152. The filaments may be composed of any suitable biocompatible material such as, but not limited to, stainless steel, platinum, platinum alloy, titanium, titanium alloys, cobalt-chromium super alloy, nickel titanium (nitinol), tungsten or other medical grade metal, polyimide or other high-modulus medical grade polymer. Filaments 152 may include flat, oval or circular cross-sections. Filaments 152 used for reinforcing layer 150 typically have a diameter or thickness between 0.0005 inches and 0.003 inches. The plurality of filaments 152 may combine individual filaments of different materials or cross-sectional shapes.

Reinforcing layer 150 may span as much as the full length from catheter body proximal end 132 to catheter body distal end 134. The length of reinforcing layer 150 and each of the braided portion and the coiled portion thereof may be determined based on the particular application for the treatment device. In one embodiment, the length of the braided portion and the coiled portion are each approximately 50 percent of the total length of reinforcing layer 150. In another embodiment, the length of the braided portion is between 50 and 90 percent of the length of reinforcing layer 150 and the length of the coiled portion is between 10 and 50 percent of the length of reinforcing layer 150. The formation of braided and coiled reinforcing layer 150 is discussed in more detail, below.

Figure 2:
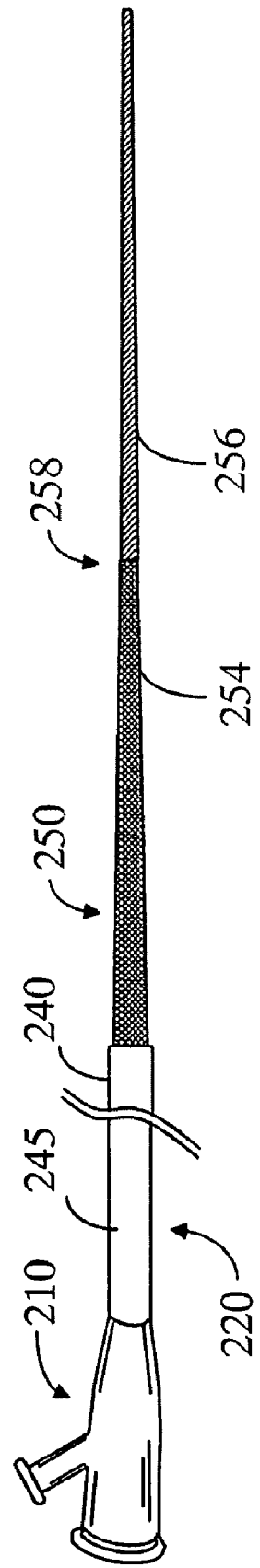
FIG. 2 illustrates one embodiment of a vascular treatment device having a braided and coiled reinforcing layer made in accordance with the present invention.

Referring now to FIG. 2, illustrated is one embodiment of a vascular treatment device 200, made in accordance with the present invention. The materials composing vascular treatment device 200 are the same as, or similar to, those discussed above for vascular treatment device 100. Vascular treatment device 200 includes proximal fitting 210 and catheter body 220. Catheter body 220 includes catheter wall portion 240 and reinforcing layer 250. For purposes of illustration, a portion of an outer layer 245 of catheter wall portion 240 has been removed to expose reinforcing layer 250.

Figure 4:
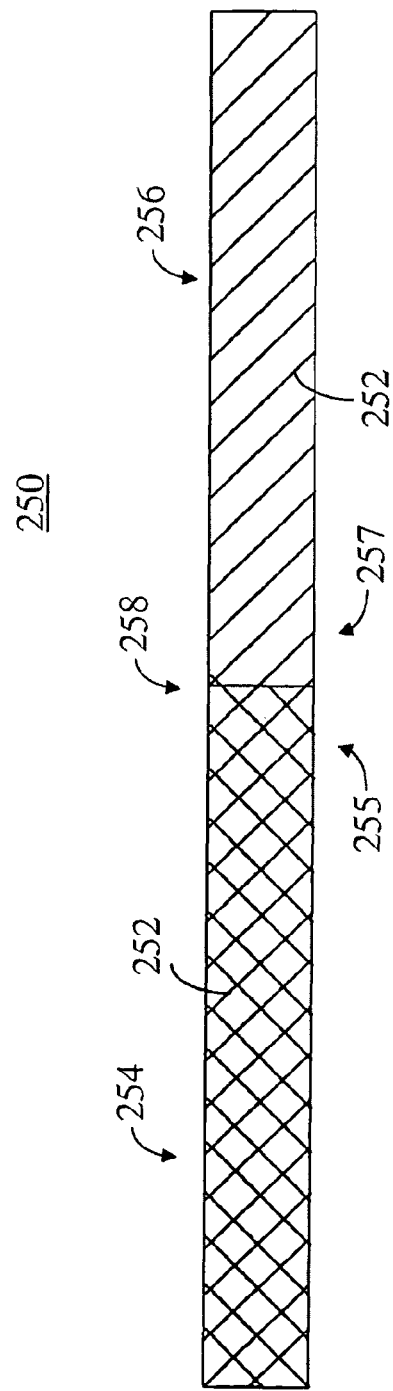
FIG. 4 illustrates a detailed view of a portion of the braided and coiled reinforcing layer depicted in FIG. 2.

Referring now to FIGS. 2 and 4, reinforcing layer 250 includes a braided portion 254 and a coiled portion 256. Coiled portion 256 is distal to braided portion 254. In one embodiment of device 200, the length of braided portion 254 is approximately 75% of the total length of catheter body 220 and the length of coiled portion 256 is approximately 25% of the remaining length. The proximal braided portion 254 of catheter body 220 has high torsional and columnar strengths sufficient to enable the vascular treatment device 200 to be steered and pushed through a patient's vascular system or other body lumen without kinking.

Reinforcing layer 250 includes a transition region 258 defined by the distal end 255 of the braided portion 254 and the proximal end 257 of the coiled portion 256. Transition region 258 is that region of the reinforcing layer where the plurality of filaments 252 transforms from a braided configuration to a multifilar coiled configuration. At least half of the plurality of filaments 252 is continuous throughout the length of reinforcing layer 250 and shifts from the braided configuration to the coiled configuration in transition region 258. The method of manufacture of catheter body 220 is discussed in more detail below.

Figure 3:
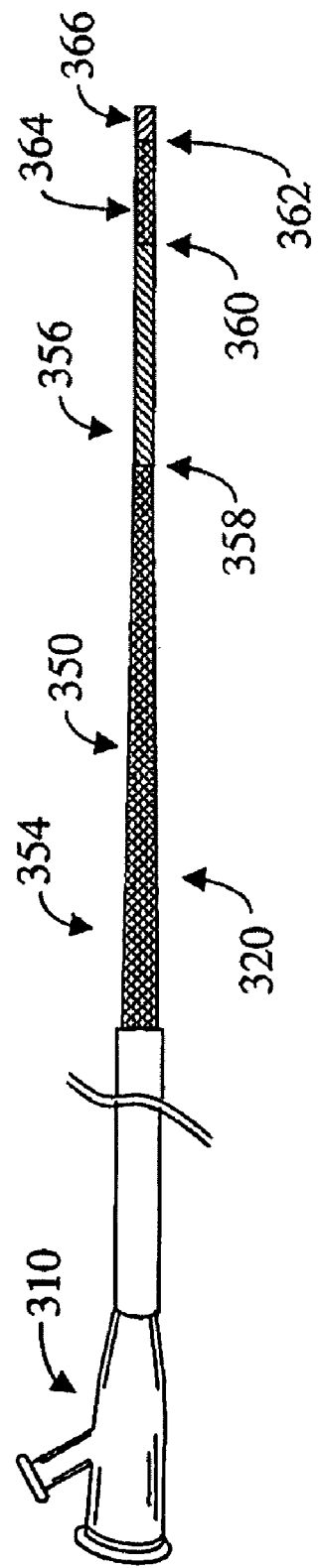
FIG. 3 illustrates another embodiment of a vascular treatment device having a braided and coiled reinforcing layer made in accordance with the present invention.

FIG. 3 illustrates another embodiment of a vascular treatment device 300 having a proximal fitting 310 and catheter body 320. In this embodiment, catheter body 320 includes a reinforcing layer 350 with multiple transition regions 358, 360, 362. Catheter body 320 includes a first transition region 358 disposed between a distal end of a first braided portion 354 and a proximal end of a first coiled portion 356. Second transition region 360 is disposed between a distal end of the first coiled portion 356 and a proximal end of a second braided portion 364. Third transition region 362 is disposed between a distal end of the second braided portion 364 and a proximal end of a second coiled portion 366.

In one embodiment of vascular treatment device 300, second braided portion 364 provides a stiffer region between two coiled portions 356, 366. In one embodiment, second braided portion 364 is located along catheter body 320 at a position that corresponds to the targeted treatment site. The respective lengths of the braided portions and the coiled portions may be predetermined based on such factors as a particular application of the treatment device, the tortuousness of the pathway to a particular treatment site to be reached or the distance the distal end must travel from the insertion site to the treatment site. The total length of the braided portions 354, 364 of device 300 is 50 to 95 percent of the length of catheter body 320 and the total length of the coiled portions 356, 366 is 5 to 50 percent. Those with skill in the art will recognize that the number and length of braided portions and coiled portions of a treatment device may vary depending on the particular application.

Figure 6A:
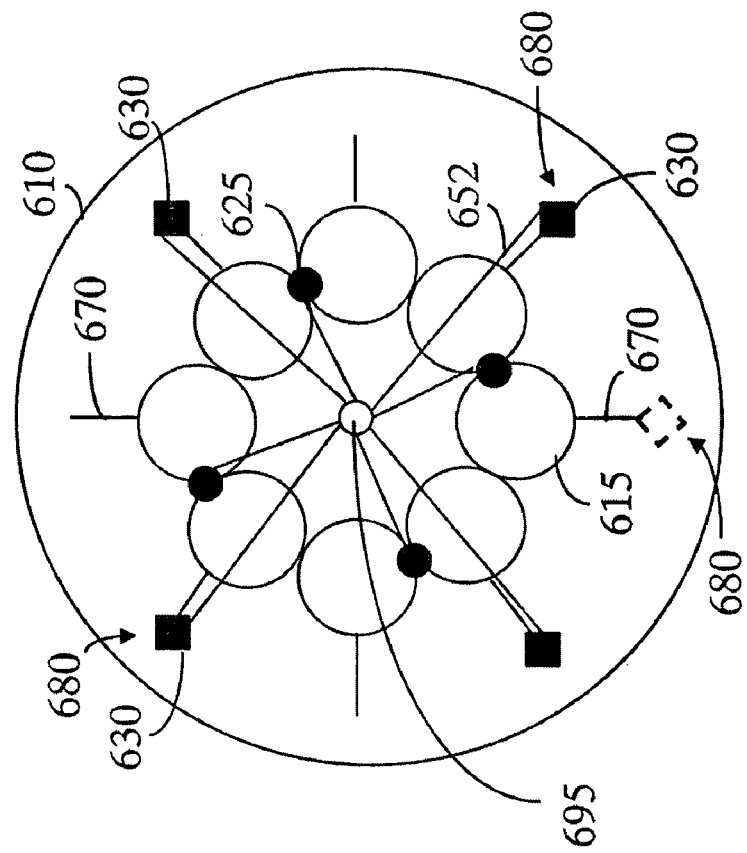

FIGS. 6A to 9B illustrate various embodiments of braiding machines 600, 800 for manufacturing braided and coiled catheter bodies. Braiding machines 600 and 800 each include a braiding configuration and a coiling configuration for forming the braided portion and the coiled portion, respectively, of a reinforcing layer such as the reinforcing layers illustrated in FIGS. 2-3. FIGS. 6A and 7A illustrate the braiding configuration of braiding machine 600 and FIGS. 8A and 9A illustrate the braiding configuration of braiding machine 800. FIGS. 6B and 7B illustrate the coiling configuration of braiding machine 600 and FIGS. 8B and 9B illustrate the coiling configuration of braiding machine 800. Throughout FIGS. 6A to 9B like reference numbers will refer to like elements.

Figure 6B:
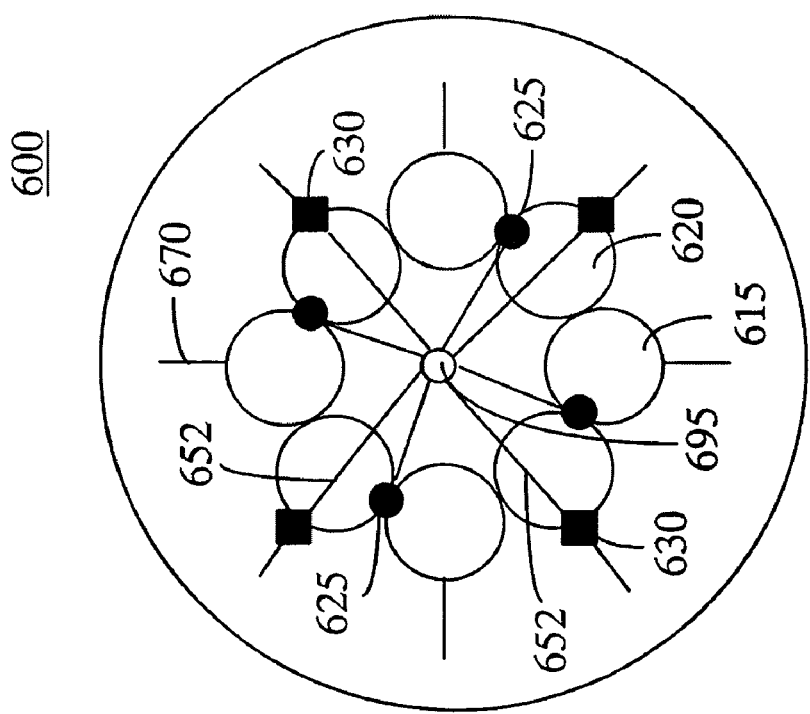

FIGS. 6A and 6B illustrate top views of braiding machine 600, and FIGS. 7A and 7B illustrate side views of braiding machine 600. Braiding machine 600 is composed of a horizontal track plate 610, a gear train comprising a plurality of counter-rotating horn gears 615, 620, and a plurality of bobbin carriers 625, 630 arranged in a "Maypole" type of braiding configuration as is known in the art. Each bobbin carrier 625, 630 includes a removable spool or bobbin 640 around which is wound a length of filament 652. Track plate 610 includes sinusoidal tracks or grooves (not shown) that extend in a circular arrangement about the axis of the machine. The bobbin carriers 625, 630 are guided around the axis of the machine in these tracks. A first track moves bobbin carriers 625 in a clock-wise direction. A second track moves bobbin carriers 630 in a counter clock-wise direction. This movement of bobbin carriers 625 in a direction opposite of carriers 630 causes the carriers to pass inwardly and outwardly around each other to interlace the attached filaments. This interlacing of filaments forms the braided portion 660 of the reinforcing layer.

FIGS. 6A and 6B illustrate a braiding machine 600 with 8 horn gears 615, 620 and 8 bobbin carriers 625, 630, one bobbin carrier for each bobbin of filament used to form the braided portion of the reinforcing layer. Those with skill in the art will recognize that the reinforcing layer of a braided and coiled catheter body may be formed from any number of filaments. For example, the braided portion of the reinforcing layer may be formed of 8 to 32 filaments. In some instances known as "double ended" or "tow" braiding configurations, the carriers may pay out multiple filaments, e.g. where two filaments are paid out from each bobbin.

FIGS. 6B and 7B illustrate the coiling configuration of the braiding machine 600. As discussed above and described with reference to FIG. 4, the reinforcing layer transitions from a braided portion to a coiled portion with continuous filaments. For use in forming the coil portion of the reinforcing layer, braiding machine 600 further includes a plurality of radial tracks 670. Radial tracks 670 extend radially from the sinusoidal tracks in track plate 610. Radial tracks 670 provide a pathway that is used to temporarily move bobbin carriers 630 out of the sinusoidal tracks to idle positions 680 away from horn gears 615, 620, leaving bobbin carriers 625 in place to continue to travel in a sinusoidal path around horn gears 615, 620. Because bobbin carriers 630 have been set apart from bobbin carriers 625, no weaving or braiding occurs while bobbin carriers 625 move through the sinusoidal track. Instead, filaments 652 from bobbins 640 on bobbin carriers 625 are merely wrapped spirally into a multifilar coil around the axis of braiding machine 600. In this embodiment, a coiled portion is formed as carriers 625 move in a clock-wise direction. In another embodiment, bobbin carriers 625 are moved to an idle position, while bobbin carriers 630 are left in place to travel around horn gears 615, 620 in a counter clock-wise direction. In an alternative embodiment, instead of moving bobbin carriers along radial tracks 670, bobbins 640 may be manually removed from bobbin carriers 630 and "parked" in an outwardly disposed position corresponding to idle positions 680.

In practice, braiding machine 600 can be used to manufacture one or a plurality of catheter bodies suitable for use in preparing a catheter. FIGS. 6A to 7B illustrate the manufacture of a single catheter body. During manufacture, the free ends of the plurality of filaments 652 are attached to a core or mandrel 695 upon which the braided and coiled catheter body is formed. Core 695 may include a layer of polymeric material 697 removably disposed around core 695. Polymeric layer 697 forms the inner polymeric layer of the catheter body (see 143 of FIG. 5). Core 695 is moved in the direction of arrow A as the braided and coiled portions are produced. Those with skill in the art will understand that the pitch of the braid and the coil may be determined by how fast core 695 moves in the upward direction in relation to the rotation speed of horn gears 615, 620, which defines the speed at which the carriers revolve in their sinusoidal path around core 695. In one embodiment, the pitch of the braid is altered along the length of a catheter by adjusting the rate of speed at which core 695 is moving longitudinally relative to the rotation speed of horn gears 615, 620. In one embodiment known to those of ordinary skill in the art, filaments 652 may be secured by pulling the over-braided catheter through a heated die to melt or soften inner polymeric layer 697 and force the filaments into embodiment therein.

Upon completion of the braided portion 660 and coiled portion 665 an outer layer of polymeric material 145 is bonded to the outer surface of the braided and coiled portions and the underlying inner polymeric layer 697. The outer layer of polymeric material may be bonded to the inner polymeric layer 697 by any suitable method such as by over-extrusion or adhesive bonding. In another embodiment, a heat shrink tube is placed around the outer polymeric layer and heated in such a manner and for a sufficient time to shrink the heat shrink tube, soften and compress the outer polymeric layer and form a thermal bond between the inner polymeric layer and the outer polymeric layer. The heat shrink tube is removed upon completion of the bonding process. Bonding the inner polymeric layer to the outer polymeric layer entraps the braided and coiled portions of the reinforcing layer.

Finally, core 695 is removed and a fitting 110, 210, 310 is affixed to the proximal end of catheter body 120, 220, 320, respectively. Other finishing steps may also be performed on catheter body 120, 220, 320, such as adding a soft distal tip, heat-forming a desired curve shape or applying any of various coatings to the inner or outer surfaces of the catheter. The addition and bonding of the outer layer 145 of polymeric material to the inner polymeric material 143 may occur any time after formation of the braid or coil. For example, in one embodiment, as soon as the braid is formed on the core the outer layer of polymeric material 145 is formed over the inner layer by a solution coating process that applies, e.g., by dipping or spraying, an uncured liquid polymer around the filaments, subsequent to which the polymer can be cured by solvent evaporation, cross-linking, or other reaction. This process may continue until the reinforcing layer is completely encased.

In some embodiments of the present invention, additional manufacturing steps may be required. In an example, the portion of filaments 652 attached to the idle bobbin carriers 625 or 630 that do not form the coiled portion may be cut at a point proximate the end of the braided portion prior to bonding the polymeric layers together. Alternatively, filaments 652 excluded from coil 665 may be laid axially (not shown) over coiled portion 665. In this fashion, at a desired location along mandrel 695 or layer 697, bobbin carriers 630 can be moved inwardly along radial tracks 670 from idle positions 680 into re-engagement with horn gears 615, 620, such that bobbin carriers 625 can resume travel in a sinusoidal path around horn gears 615, 620 to begin forming another braided portion. Thus, any number of braided and coiled regions can be formed sequentially without severing reinforcing filaments 652.

Referring to FIGS. 8A to 9B, FIGS. 8A and 8B illustrate top views of braiding machine 800. FIGS. 9A and 9B illustrate side views of braiding machine 800. Braiding machine 800 is similar in many respects to braiding machine 600. Elements in common will not be described in detail herein. The braiding configuration of machine 800 is the same as that of machine 600. Braiding machine 800 differs from machine 600 in the manner in which the coiled portion is formed and the additional machine elements used for forming the coiled portion.

Braiding machine 800 includes a circular pathway 875 for forming the coiled portion of the reinforcing layer. In this embodiment, the braided portion 860 of the reinforcing layer is formed on the core 695 in the same manner as braided section 660. However, to form coiled portion 865 bobbin carriers 625, 630 move from horn gears 615, 620 to the circular coil-forming pathway 875 via radial pathways 670. Once the bobbin carriers are positioned in the coil pathway, the bobbin carriers move along the circular coil pathway in the direction of arrow B, impelled by a rotational drive mechanism (not shown) that may engage bobbin carriers 625, 630 from either above or below horizontal track plate 610. In this embodiment, as core 695 moves upward relative to the circular movement of bobbin carriers 625, 630, a coil portion 865 is formed wherein all of the filaments are wrapped around the core in the same direction. As illustrated, the coil portion 865 is formed as the bobbin carriers move in a clock-wise direction. In another embodiment, the bobbin carriers move in a counter clock-wise direction. In another embodiment, only bobbin carriers 630 are moved to circular pathway 875 while bobbin carriers 625 remain engaged with horn gears 615, 620. Then, carriers 630 are moved around circular pathway 875 in the same rotational direction, and typically at the same rotational speed as carriers 625 to form a multifilar coil comprising all of filaments 652.

In one embodiment, the bobbin carriers move from coil-forming pathway 875 back to the horn gears via radial tracks 670 to form another braided portion immediately after a coiled portion. Those with skill in the art will appreciate that the machines described herein may be used to form a continuous length of reinforcing layer having a plurality of alternating braided and coiled portions. This length then may be divided to form numerous individual catheter bodies that include the desired braided and coiled portions.

Figure 10:
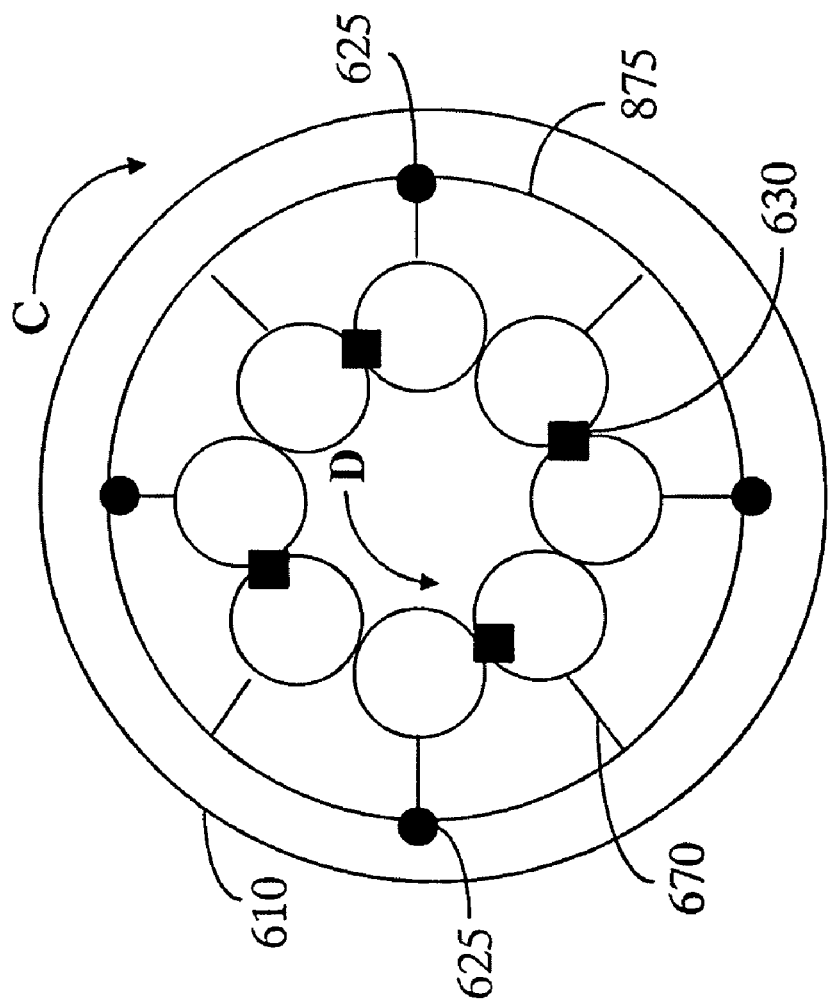
FIG. 10 is a schematic illustration of yet another embodiment of a braiding machine in accordance with the present invention.

Braiding machine 800 may also be used to form a coiled portion having a first coil formed in the clock-wise direction and a second coil formed in the counter clock-wise direction. In this embodiment, the first coil and second coil overlap but are not interwoven as would define a braided portion. To form this overlapping counter-coiled portion, a first plurality of bobbin carriers is moved to the coiled pathway and a second plurality of bobbin carriers remain in the horn gears. In an example, illustrated in FIG. 10, bobbin carriers 625 are moved to the coil pathway 875 and bobbin carriers 630 remain in horn gears 620. Then, to form the overlapping coil, bobbin carriers 625 move around coil pathway 875 in a clock-wise direction (arrow C) and bobbin carriers 630 move around the horn gears in a counter clock-wise direction (arrow D).

Figure 8B:
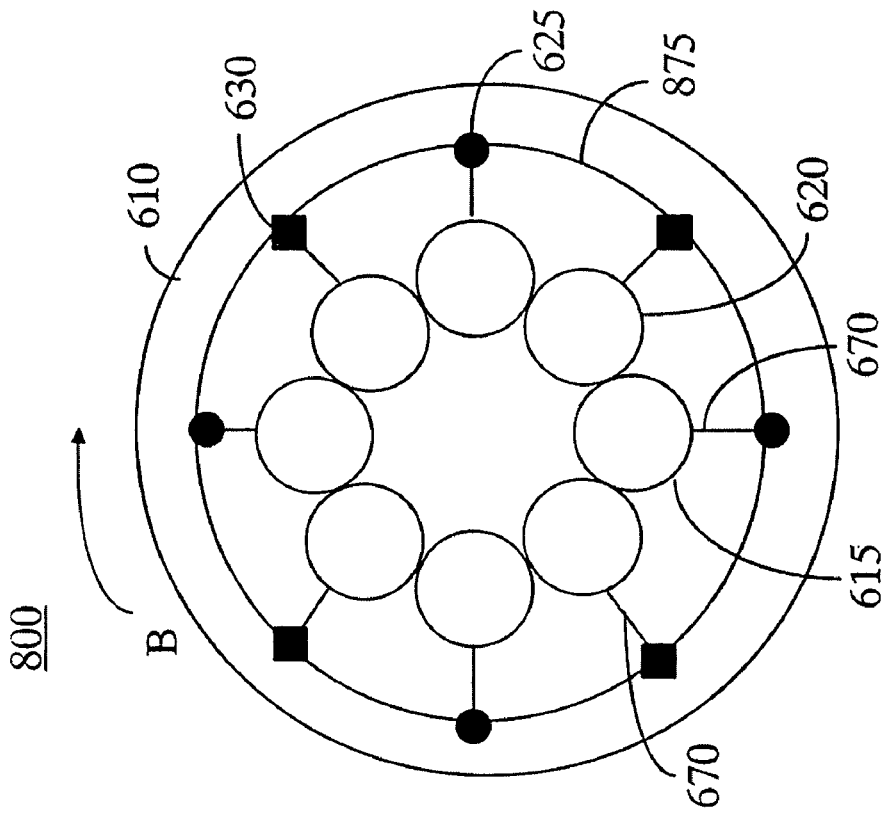
Figure 8A:
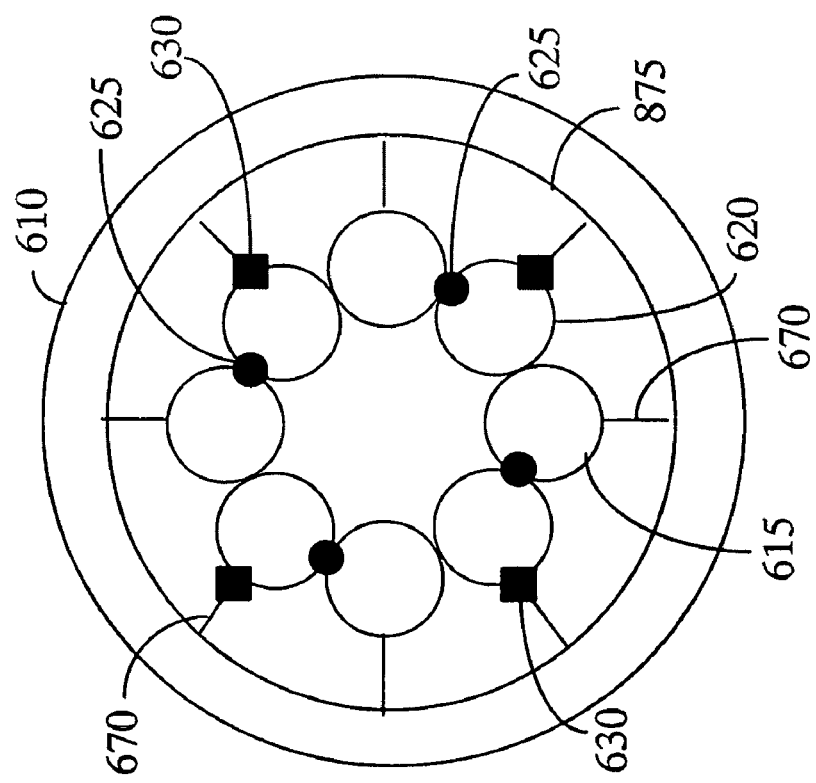

In another embodiment of braiding machine 800, circular pathway 875 and radial tracks 670 are disposed radially inward (not shown) from the sinusoidal tracks associated with the horn gears instead of being disposed radially outward as illustrated in FIGS. 8A and 8B. This embodiment is especially useful where the reinforcing layer is composed of 16 to 32 filaments. Having the coil pathway located inward of the horn gear track provides for a smaller horizontal deck on which the horn gears and bobbin carriers move. In another embodiment, the braiding machine includes both a circular pathway disposed radially inward and a circular pathway disposed radially outward with respect to the sinusoidal tracks associated with the horn gears. In this embodiment, bobbin carriers may be moved via radial tracks to either inner or outer circular tracks. The bobbin carriers can be divided, as may be desired, between the inner and outer circular tracks.

In yet another embodiment of the braiding machine made in accordance with the present invention, the reinforcing layer is formed directly on the outer surface of the core or mandrel. In this embodiment, the core or mandrel does not include a removable polymeric layer for forming the inner layer.

Removing the mandrel after applying an outer layer then exposes reinforcing filaments 652 to the inner lumen 122 to form a thin-walled catheter shaft, as taught in U.S. Pat. No. 5,964,971 to Lunn.

Figure 11:
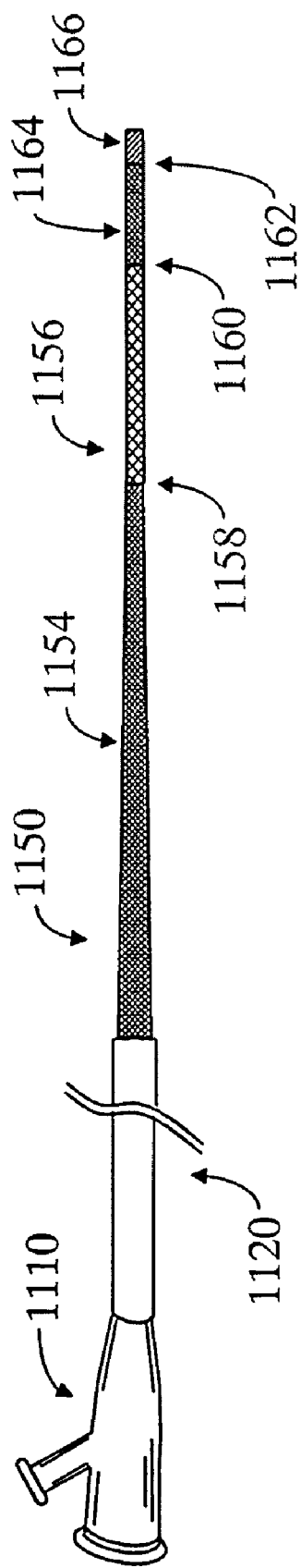
FIG. 11 illustrates another embodiment of a vascular treatment device having a braided reinforcing layer made in accordance with the present invention

FIG. 11 illustrates another embodiment of a vascular treatment device 1100 that includes proximal fitting 1110, catheter body 1120 and a braided reinforcing layer 1150 that includes first full complement braid portion 1154, first partial complement braid portion 1156 and a second full complement braid portion 1164. A full complement braid portion comprises a braid portion manufactured using a full set of filaments as determined by the number of bobbin carriers utilized for preparing the braid. In this embodiment, reinforcing layer 1150 includes a variable strand construction that provides varying physical properties along the length of the catheter. In this embodiment, the relative stiffness and flexibility of the catheter changes abruptly as the number of filaments composing the reinforcing layer either increases or decreases. The method of manufacturing the variable strand reinforcing layer is described in more detail below.

Figure 13A:
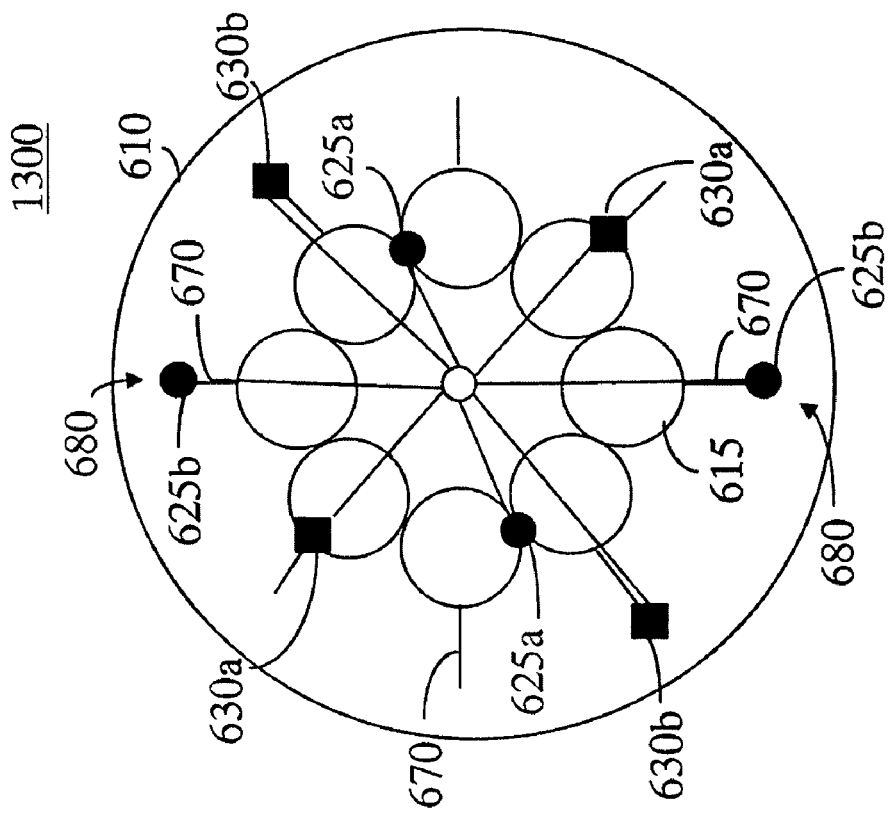
Figure 13B:
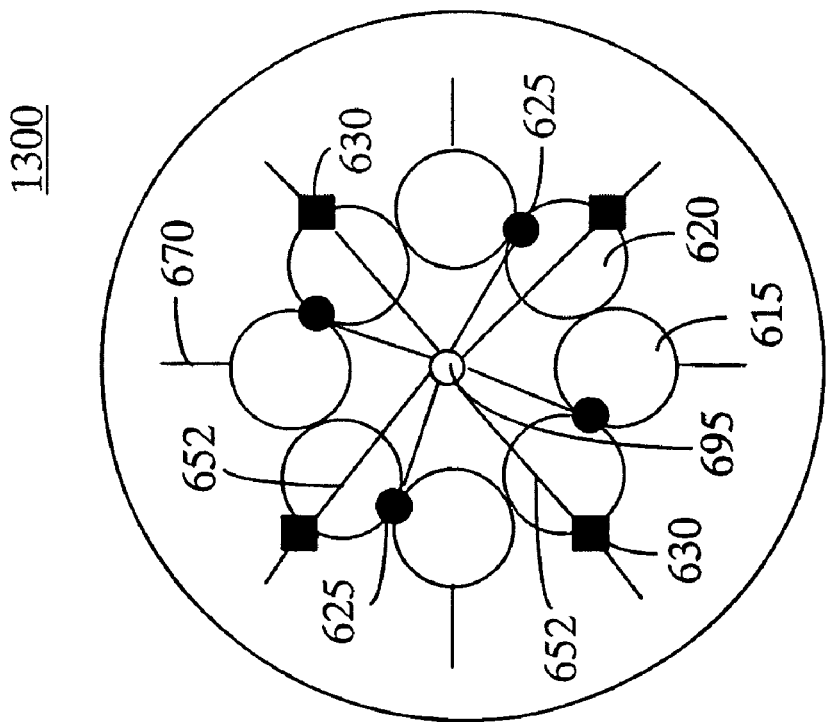

FIGS. 13A and 13B illustrate a braiding machine 1300 having eight bobbin carriers. Using braiding machine 1300 as an example, a full set of filaments includes 8 filaments, each carried by a single bobbin carrier. In this example, a full complement braid portion comprises eight interwoven filaments. Thus, where the braiding machine includes sixteen bobbin carriers, a full complement braid portion comprises sixteen interwoven filaments. A partial complement braid portion is defined as a braid portion that is woven from less than the full complement of filaments. Thus, in the example of eight bobbin carriers, a partial complement braid portion may have from two to seven interwoven filaments. In the example of sixteen bobbin carriers, a partial complement braid portion may have from two to fifteen interwoven filaments. More complex braid examples of the invention can be made by mounting more than one bobbin on each bobbin carrier, and/or by winding more than one filament on each bobbin, and such techniques are known to those of skill in the art. In catheters of the invention, the full complement braid portion may comprise between 2 and 144 filaments.

Figure 12:
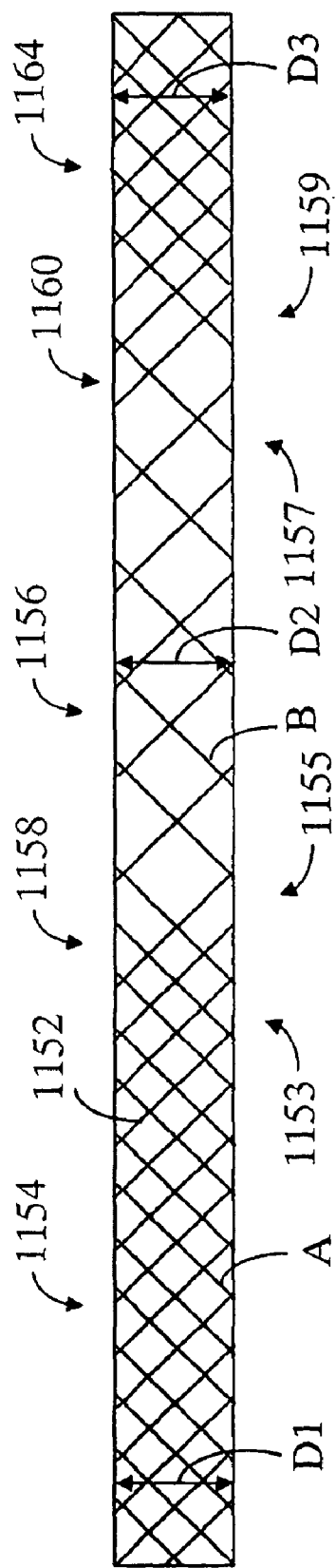
FIG. 12 illustrates a detailed view of a portion of one embodiment of a braided reinforcing layer shown in FIG. 11 and made in accordance with the present invention.

Referring to FIGS. 11 and 12, catheter body 1120 includes a reinforcing layer 1150 with transition regions 1158, 1160 disposed between the full complement braid portions 1154, 1164 and the partial complement braid portion 1156. First transition region 1158 is disposed between a distal end 1153 of a first full complement braid portion 1154 and a proximal end 1155 of a first partial complement braid portion 1156. Second transition region 1160 is disposed between a distal end 1157 of the first partial complement braid portion 1156 and a proximal end 1159 of a second full complement braid portion 1164.

Transition region 1158 is that region of the reinforcing layer where the plurality of filaments 1152 transforms, as viewed from left to right in the drawing, from a full complement braid configuration to a partial complement braid configuration. Transition region 1160 is that region of the reinforcing layer where the plurality of filaments 1152 transforms, as viewed from left to right in the drawing, from the partial complement braid configuration back to the full complement braid configuration.

FIG. 12 also illustrates that the pitch angle "A" of the filaments 1152 composing the full complement braid portion 1154 is substantially equal to the pitch angle "B" of the filaments 1152 composing the partial complement braid portion 1156. The term pitch angle is used herein to mean the angle formed between a filament and the longitudinal axis of the tubular reinforcing layer. In one embodiment, the pitch angle in both the full complement braid portions and the adjacent partial complement braid portions is held constant during manufacture by moving the mandrel 695 at a constant rate relative to the rotation rate of the bobbins during the braiding process.

In one embodiment, at least half of the plurality of filaments 1152 is continuous throughout the length of reinforcing layer 1150 and shifts from the full complement braid configuration to the partial complement braid configuration in transition region 1158 and then back to the full complement braid configuration in transition region 1160.

FIG. 12 illustrates that, in one embodiment of reinforcing layer 1150, the spacing between filaments 1152 in partial complement braid portion 1156 increases as the number of filaments decreases. This reduction in the number of filaments creates an open weave. This open weave provides a more flexible reinforcing layer as compared to the full complement braid portions 1154, 1164. Similarly, as the number of filaments increases from a partial complement to a full complement, the spacing between the filaments decreases and the weave becomes a closer weave. The closer weave creates a less flexible reinforcing layer as compared to partial complement braid portion 1156.

FIG. 12 also illustrates that the diameter D1 of the full complement braid portion remains substantially constant with the diameter D2 of the partial complement braid portion as the reinforcing layer 1150 transitions between the full complement braid portion 1154 and the partial complement braid portion 1156. FIG. 12 also illustrates that the diameter D3 of full complement braid portion 1164 is substantially equal to diameters D1 and D2.

FIG. 11 further illustrates that a catheter body having a reinforcing layer with variable strand construction may also include a coiled portion similar to those described above. In one embodiment, reinforcing layer 1150 includes a coiled portion 1166 positioned at a distal end of catheter 1100. A third transition region 1162 is disposed between a distal end of the second full complement braid portion 1164 and a proximal end of coiled portion 1166. Transition region 1162 is that region of the reinforcing layer where the plurality of filaments 1152 transforms, as viewed from left to right in the drawing, from a full complement braid configuration to a multifilar coiled configuration.

In one embodiment of vascular treatment device 1100, the proximal full complement braid portion 1154 of catheter body 1120 has high torsional and columnar strengths sufficient to enable the vascular treatment device 1100 to be steered and pushed through a patient's vascular system or other body lumen without kinking. In contrast, first partial complement braid portion 1156 provides a more flexible region between two full complement braid portions 1154, 1164. In one embodiment, first partial complement braid portion 1156 is located along catheter body 1120 at a position that corresponds to the targeted treatment site. In another embodiment, first partial complement braid portion 1156 is located along catheter body 1120 at a position that corresponds to a bend in the vasculature proximal to and/or adjacent to the treatment site. The respective lengths of the full complement braid portions, the partial complement braid portions and the coiled portions, if present, may be predetermined based on such factors as a particular application of the treatment device, the tortuousness of the pathway to a particular treatment site to be reached or the distance the distal end must travel from the insertion site to the treatment site. Those with skill in the art will recognize that the order, number and length of full complement and partial complement braid portions and coiled portions of a treatment device may vary depending on the particular application. The number and order of full complement braid portions and partial complement braid portions may vary depending on, for example, the physical properties of the treatment site and the vascular pathway leading to the treatment site.

Referring to FIGS. 13A to 14B, FIGS. 13A and 13B illustrate top views of braiding machine 1300. FIGS. 14A and 14B illustrate side views of braiding machine 1300. Braiding machine 1300 is similar in many respects to braiding machine 600. Elements in common have common reference numbers and will not be described in detail herein. The braiding configuration of machine 1300 is the same as that of machine 600. Braiding machine 1300 differs from machine 600 in the manner in which the partial complement braid portion is formed.

FIGS. 13A and 13B illustrate a braiding machine 1300 with 8 horn gears 615, 620 and 8 bobbin carriers 625, 630, one bobbin carrier for each bobbin of filament used to form the braided portion of the reinforcing layer. FIGS. 13A and 14A illustrate the full complement braid configuration where each of the eight bobbin carriers are positioned to travel around the sinusoidal track to form a full complement braid portion 1154 with eight interwoven filaments 652.

FIGS. 13B and 14B illustrate the partial complement braid configuration of braiding machine 1300. As discussed above and described with reference to FIGS. 11 and 12, reinforcing layer 1150 transitions from a full complement braid portion 1154 to a partial complement braid portion 1156 with continuous filaments 652. For use in forming the partial complement braid portion 1156 of the reinforcing layer, braiding machine 1300 further includes a plurality of radial tracks 670. Radial tracks 670 extend radially from the sinusoidal tracks in track plate 610. Radial tracks 670 provide a pathway that is used to temporarily move a first portion of bobbin carriers 625b, 630b out of the sinusoidal tracks to idle positions 680 away from horn gears 615, 620, leaving a second portion of bobbin carriers 625a, 630a in place to continue to travel in a sinusoidal path around horn gears 615, 620 and to form the partial complement braid portion 1156.

As illustrated in FIG. 13B, two each of bobbin carriers 625b, 630b are moved to radial tracks 670 and the remaining four bobbin carriers 625a, 630a are left to travel in the clockwise or counter-clockwise direction to form a partial complement braid having four filaments. As the remaining bobbin carriers travel around the track, the filaments 652a (FIG. 14B) of the first portion of bobbin carriers 625b, 630b in idle positions 680 pays out filament 652 axially. At a desired location along mandrel 695 or layer 697, bobbin carriers 625b, 630b can be moved inwardly along radial tracks 670 from idle positions 680 into re-engagement with horn gears 615, 620, such that bobbin carriers 625b, 630b can resume travel in a sinusoidal path around horn gears 615, 620 to begin forming another full complement braid portion 1164. Bobbin carriers 625b, 630b may be returned to the sinusoidal path automatically or manually. In an alternative embodiment, instead of moving bobbin carriers 625b, 630b along radial tracks 670, bobbins 640 may be manually removed from bobbin carriers 625b, 630b and "parked" in an outwardly disposed position corresponding to idle positions 680. In one embodiment, during the formation of the full complement braid portion and the partial complement braid portion, the rate of movement of mandrel 695 remains substantially constant relative to the rotation of the bobbin carriers in the sinusoidal path in track plate 610. In this embodiment, the pitch angle of the continuous filaments 652 that form the full complement braid portion 1154, 1164 and the partial complement braid portion 1156 remains substantially constant.

In some embodiments of the present invention, additional manufacturing steps may be required. In an example, the portion of filaments 652a attached to the idle bobbin carriers 625 or 630 that do not form the partial complement braid portion may be cut at a point proximate the end of the braided portion prior to bonding the polymeric layers together. Alternatively, filaments 652a excluded from partial complement braid portion 1156 may be left in their axially laid positions over partial complement braid portion 1156 as shown in FIG. 14B, prior to bonding the polymeric layers together. In another embodiment, a coiled portion 1166 may be added in a manner the same as or similar to that described above and illustrated in FIGS. 6B and 7B.

Figure 15:
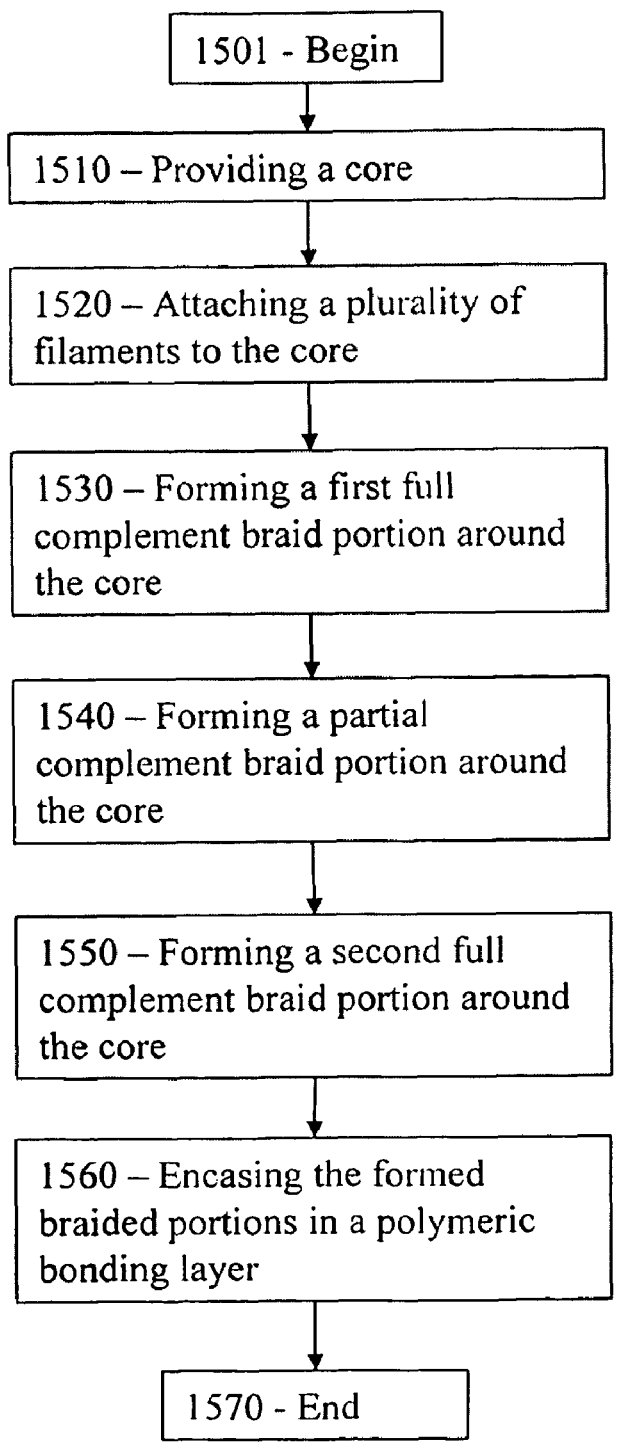
FIG. 15 is a flow chart of one embodiment of a method of manufacturing a braided elongate member, in accordance with the present invention.

FIG. 15 illustrates a flow chart of one embodiment of a method of manufacturing a braided elongate member having a variable strand reinforcing layer. Method 1500 may be performed on any of the braiding machine embodiments described above and illustrated in FIGS. 6A to 7B and 13A to 14B.

Method 1500 begins at block 1501. A core 695 is provided on a braiding machine 600, 1300 (Block 1510). At least one braided catheter body having at least one full complement braid portion and at least one partial complement braid portion is formed on core 695. In one embodiment, a first polymeric layer 143, 697 is removably mounted about the core 695 prior to forming the braided catheter body. A plurality of filaments 152, 652 is attached to a first end of the core (Block 1520). Next, the plurality of filaments 152, 652 is formed into at least one full complement braid portion 1154 surrounding the core (Block 1530). The braided portion may be formed by braiding machine 600, 1300.

A portion of the plurality of filaments that form the full complement braid portion are removed from the braiding path and a remaining portion of the plurality of filaments that form full complement braid portion 1154 are then sequentially and continuously used to form a partial complement braid portion 1156 surrounding the core (Block 1540). As described in detail above, the at least one full complement braid portion 1154 is transformed to the partial complement braid portion 1156 through a transition region 1158. In one embodiment, after the removed portion of filaments has been laid axially along the outside of partial complement braid portion 1156, the removed portion of filaments is re-inserted into the weave by placing bobbin carriers 625b, 630b back into the braiding track where they can resume sinusoidal travel to form another full complement braid portion 1164 (Block 1150). Next, the formed braided reinforcing layer 1150 is encased in a polymeric bonding layer by bonding a second polymeric layer 145 to the first polymeric layer (Block 1160). Method 1500 ends at 1170.

Formation of the braided portions for method 1500 may be accomplished by any one or more of the processes described above and illustrated in FIGS. 6A to 7B and 13A to 14B. In one embodiment the at least one full complement braid portion is formed by moving a first plurality of bobbin carriers 625 in a clock-wise direction and moving a second plurality of bobbin carriers 630 in a counter clock-wise direction.

In another embodiment, the at least one partial complement braid portion is formed by moving at least one of the first plurality of bobbin carriers 625b, 630b to an idle position 680 and moving the remaining bobbin carriers 625a, 630a in either a clock-wise or counter clock-wise direction.

In yet another embodiment, at least one coiled portion is formed subsequent to forming one of a full complement and/or a partial complement braid portion using continuous filaments by moving the first plurality 625 and the second plurality 630 of bobbin carriers to a circular pathway 875 and moving the first plurality and the second plurality of bobbin carriers in either a clock-wise or counter clock-wise direction.

While the invention has been described with reference to particular embodiments, it will be understood by one skilled in the art that variations and modifications may be made in form and detail without departing from the spirit and scope of the invention.

What is claimed is:

1. A catheter comprising an elongate catheter body having a reinforcing layer encased within a polymeric bonding layer, wherein the reinforcing layer comprises a continuous plurality of filaments forming a first full complement braid portion, a partial complement braid portion connected to a distal end of the first full complement braid portion through a first transition region, and a second full complement braid portion connected to a distal end of the partial complement braid portion through a second transition region.

2. The catheter of claim 1 further comprising a coiled portion having a proximal end connected through a third transition region to a distal end of the second full complement braid portion.

3. The catheter of claim 1 wherein the reinforcing layer comprises one or more materials selected from the group consisting of stainless steel, platinum, platinum alloy, titanium, titanium alloys, cobalt-chromium super alloy, nickel titanium (nitinol), tungsten, medical grade metal, polyimide and high-modulus medical grade polymer.

4. The catheter of claim 3 wherein the reinforcing layer comprises only one of the materials selected from the group consisting of stainless steel, platinum, platinum alloy, titanium, titanium alloys, cobalt-chromium super alloy, nickel titanium (nitinol), tungsten, medical grade metal, polyimide and high-modulus medical grade polymer.

5. The catheter of claim 1 wherein the polymeric bonding layer comprises an inner layer and an outer layer, the outer layer bonded to the inner layer to encase the reinforcing layer.

6. The catheter of claim 1 wherein the polymeric bonding layer comprises one or more materials selected from the group consisting of polyamide, polyimide, polyolefin, polyethylene, polypropylene, polyurethane, polyethylene block amide copolymer (PEBA), fluoropolymers, polytetrafluoroethylene (PTFE), fluorinated ethylene propylene (FEP), and perfluoroalkoxy (PFA).

7. The catheter of claim 1 wherein the plurality of filaments forming the first full complement braid portion comprises between 2 and 144 filaments.

8. The catheter of claim 7 wherein the partial complement braid portion lacks one or more filaments that are included within the first full complement braid portion.

9. The catheter of claim 1 wherein a pitch angle of the filaments forming the first full complement braid portion is substantially equal to a pitch angle of the filaments forming the partial complement braid portion.

10. The catheter of claim 1 wherein a diameter of the first full complement braid portion is substantially equal to a diameter of the partial complement braid portion.

11. A catheter comprising an elongate body encapsulating an elongate reinforcing layer wherein the reinforcing layer comprises a plurality of filaments extending continuously along the length of the reinforcement layer,
wherein the plurality of filaments transitions from a first full complement braid configuration to a partial complement braid configuration; and
wherein the plurality of filaments further transitions from the partial complement braid configuration to a second full complement braid configuration.

12. The catheter of claim 11 wherein the partial complement braid portion lacks one or more filaments that are included within the first full complement braid portion.

13. The catheter of claim 11 further comprising an open lumen extending through the catheter body.

14. The catheter of claim 11 wherein the elongate body comprises a polymer.

15. The catheter of claim 11 wherein the elongate body comprises an inner layer and an outer layer, the outer layer bonded to the inner layer to encapsulate the reinforcing layer.

16. The catheter of claim 11 wherein the reinforcing layer extends substantially the full length of the elongate body.

17. The catheter of claim 11 wherein a diameter of the first full complement braid portion is substantially equal to a diameter of the partial complement braid portion.

18. A method of manufacturing a braided catheter, the method comprising:
providing a core comprising a first polymeric layer removably mounted about a mandrel, and wherein the plurality of filaments is formed into braid portions about the core;
attaching a plurality of filaments to a first end of the core;
forming the plurality of filaments into a first full complement braid portion surrounding the core;
forming a portion of the plurality of filaments into a partial complement braid portion surrounding the core, wherein the first full complement braid portion is transformed to the partial complement braid portion through a first transition region;
forming a portion of the plurality of filaments into a second full complement braid portion, wherein the partial complement braid portion is transformed to the second full complement braid portion through a second transition region; and
encasing the formed braid portions in a polymeric bonding layer by bonding a second polymeric layer to the first polymeric layer.

19. The method of claim 18 wherein forming the first full complement braid portion and the partial complement braid portion comprises forming the first full complement braid portion and the partial complement braid portion using a. braiding machine.

20. The method of claim 19 wherein the braiding machine comprises a first braiding configuration for forming the full complement braid portion and a second braiding configuration for forming the partial complement braid portion.

21. The method of claim 20 wherein the braiding machine includes a first plurality of bobbin carriers and a second plurality of bobbin carriers.

22. The method of claim 21 wherein forming the first full braid portion comprises moving the first plurality of bobbin carriers in a clock-wise direction and moving the second plurality of bobbin carriers in a counter clock-wise direction.

23. The method of claim 22 wherein the partial complement braid portion is formed by moving at least one of the first plurality or the second plurality of bobbin carriers to an idle position and moving the remaining of the first plurality of bobbin carriers in a clock-wise direction and the remaining second plurality of bobbin carriers in the counter clock-wise direction.

24. The method of claim 19 wherein forming the first full complement braid portion and the partial complement braid portion further comprises maintaining a constant pitch angle in the first full complement braid portion and the partial complement braid portion.

25. The method of claim 24 wherein maintaining the constant pitch angle in the first full complement braid portion and the partial complement braid portion comprises moving the core through the braiding machine at a constant rate.

26. The method of claim 19 wherein forming the first full complement braid portion and the partial complement braid portion further comprises maintaining a substantially constant diameter in the at least one full complement braid portion and the at least one partial complement braid portion.

* * * * *